United States Patent
Govari et al.

(10) Patent No.: US 8,827,993 B2
(45) Date of Patent: Sep. 9, 2014

(54) GATED SAMPLING OF ELECTROCARDIOGRAM SIGNALS DURING ABLATION WAVEFORM ZERO-CROSSING

(75) Inventors: Assaf Govari, Haifa (IL); Andres Claudio Altmann, Haifa (IL); Yaron Ephrath, Karkur (IL)

(73) Assignee: Biosense Webster (Israel) Ltd., Yokneam (IL)

(*) Notice: Subject to any disclaimer, the term of this patent is extended or adjusted under 35 U.S.C. 154(b) by 353 days.

(21) Appl. No.: 13/495,084

(22) Filed: Jun. 13, 2012

(65) Prior Publication Data

US 2013/0338520 A1  Dec. 19, 2013

(51) Int. Cl.
*A61B 18/04* (2006.01)

(52) U.S. Cl.
USPC .......................................... 606/33

(58) Field of Classification Search
CPC ........... A61B 18/1492; A61B 2018/00839; A61B 2018/00577; A61B 2018/00357
USPC ...................... 600/522; 606/32–33
See application file for complete search history.

(56) References Cited

U.S. PATENT DOCUMENTS

| 6,647,289 B2 | 11/2003 | Prutchi |
| 7,894,885 B2 | 2/2011 | Bartal et al. |
| 2008/0004534 A1 | 1/2008 | Gelbart et al. |
| 2009/0306641 A1 | 12/2009 | Govari et al. |
| 2010/0023004 A1 | 1/2010 | Francischelli et al. |
| 2012/0029504 A1* | 2/2012 | Afonso et al. .................. 606/34 |

OTHER PUBLICATIONS

European Search Report for corresponding Patent Application No. EP13171717 dated Sep. 27, 2013.

* cited by examiner

*Primary Examiner* — Brian T Gedeon
(74) *Attorney, Agent, or Firm* — Louis J. Capezzuto

(57) ABSTRACT

An apparatus includes detection circuitry and gating circuitry. The detection circuitry is configured to sense a radio frequency (RF) ablation signal that is applied to a heart by an intra-body probe, and to identify time intervals during which an amplitude of an ablation signal is within a predefined window. The gating circuitry is configured to gate an electrocardiogram (ECG) signal acquired in the heart, such that the ECG signal is sampled only within the identified time intervals.

9 Claims, 2 Drawing Sheets

GATED SAMPLING OF ELECTROCARDIOGRAM SIGNALS DURING ABLATION WAVEFORM ZERO-CROSSING

FIELD OF THE INVENTION

The present invention relates generally to cardiac therapy, and particularly to methods and systems for detecting cardiac signals during RF ablation therapy.

BACKGROUND OF THE INVENTION

Various techniques are known in the art for isolating between different signals used in cardiac therapy. For example, U.S. Patent Application Publication 2009/0306641, whose disclosure is incorporated herein by reference, describes an array of notch filters for keeping Radio Frequency (RF) ablation energy from penetrating through a pacing circuit. The array comprises two branches of notch filters with high impedance in the frequency range that is used for ablation: one branch protecting the signal path between the pacing circuit and the catheter tip, and the other protecting the return path. The filters have low impedance at the pacing frequency, thus permitting pacing to proceed simultaneously with ablation.

U.S. Pat. No. 7,894,885, whose disclosure is incorporated herein by reference, describes a method for monitoring an electrocardiogram (ECG) signal of a subject. The method includes digitally sampling an average signal from at least a first ECG electrode, determining an average interference frequency, and digitally sampling and buffering a raw ECG signal from at least a second ECG electrode. The method further includes filtering the raw ECG signal to generate a residual signal, calculating, based on the residual signal, a first amplitude and a first phase shift of a primary interference signal at the average interference frequency and a second amplitude and a second phase shift of one or more harmonic interference signals at respective multiples of the average interference frequency, and digitally subtracting the primary interference signal and the harmonic interference signals from the raw ECG signal so as to generate and output a clean ECG signal.

U.S. Pat. No. 6,647,289, whose disclosure is incorporated herein by reference, describes a cardiorespiratory monitor that generates bioimpedance sensing signals that produce substantially no interference with bioimpedance signals generated by implanted devices. The monitor detects the bioimpedance signal generated by the implanted device. The monitor analyzes this detected signal to generate a bioimpedance sensing signal that will not interfere with the sensed signal. For instance, if the monitor produces a pulsed sensing signal, the pulses are delivered in an interval of the detected signal where no pulses are present. Similarly, if the monitor produces a high frequency AC sensing signal, the zero crossings of the AC sensing signal are positioned during the delivery of a pulse by the implanted device.

SUMMARY OF THE INVENTION

An embodiment of the present invention that is described herein provides an apparatus including detection circuitry and gating circuitry. The detection circuitry is configured to sense a radio frequency (RF) ablation signal that is applied to a heart by an intra-body probe, and to identify time intervals during which an amplitude of an ablation signal is within a predefined window. The gating circuitry is configured to gate an electrocardiogram (ECG) signal acquired in the heart, such that the ECG signal is sampled only within the identified time intervals.

In some embodiments, the detection circuitry includes a Schmidt Trigger configured to generate a gating signal when the amplitude of the RF ablation signal is within the predefined window. In other embodiments, the gating circuitry includes an analog-to-digital converter that is gated to sample the electrocardiogram (ECG) signal only during the identified time intervals.

In other embodiments, the apparatus also includes a tunable load for setting the predefined window, such that the Schmidt Trigger is configured to generate the gating signal based on a comparison between the amplitude of the RF ablation signal and a voltage on the tunable load.

There is also provided, in accordance with an embodiment of the present invention, a method including sensing a radio frequency (RF) ablation signal that is applied to a heart by an intra-body probe. Time intervals are identified during which an amplitude of an ablation signal is within a predefined window. An electrocardiogram (ECG) signal acquired in the heart is gated such that the ECG signal is sampled only within the identified time intervals.

There is also provided, in accordance with an embodiment of the present invention, a cardiac ablation apparatus including a radio frequency (RF) ablation generator, at least one intra-body probe, and a detection and gating unit. The radio frequency (RF) ablation generator is configured to generate an RF ablation signal. The at least one intra-body probe is configured to apply the RF ablation signal in a heart and to acquire an electrocardiogram (ECG) signal in the heart. The detection and gating unit further includes detection circuitry and gating circuitry. The detection circuitry is configured to sense the RF ablation signal that is applied by the intra-body probe, and to identify time intervals during which an amplitude of the RF ablation signal is within a predefined window. The gating circuitry is configured to gate the ECG signal acquired in the heart, such that the ECG signal is sampled only within the identified time intervals.

The present invention will be more fully understood from the following detailed description of the embodiments thereof, taken together with the drawings in which:

DETAILED DESCRIPTION OF EMBODIMENTS

Overview

Radio frequency catheter ablation (RFCA) is a known technique for the treatment of various cardiac conditions. In this procedure, an intra-body probe, typically a catheter, comprising an ablation electrode at the distal tip is percutaneously inserted into the cardiovascular system and navigated through the cardiovascular system into the heart to the target zone with the damaged tissue to be ablated. An RF signal is applied to the ablation electrode for heating the heart tissue and creating a small non-conducting lesion, which locally removes the parasitic conducting paths of the heart's electrical signals causing tachyarrhythmias and atrial fibrillation.

Monitoring electrocardiogram (ECG) signals while simultaneously applying the RF ablation signal is beneficial for assessing in real time if the procedure improved the heart function, or if more RF ablation needs to be delivered. However, the RF ablation signal itself induces high power, high frequency currents that interfere with the detection of the electrocardiogram signals due to leakage of the RF ablation signal into the detector, which corrupts the ECG signals.

Embodiments of the present invention that are described herein provide improved methods and systems for sensing cardiac ECG signals in the presence of an RF ablation signal. In some embodiments, the RF ablation signal is applied and the ECG signal is received through the use of a common electrode. The ECG signal may be corrupted by leakage of the strong RF signal into the ECG detector.

In the disclosed embodiments, detection circuitry identifies time intervals during which the amplitude of the RF ablation signal is small—Around the zero crossings of the RF ablation signal. Gating circuitry gates the acquisition of the ECG signal, such that the ECG signal is acquired only during the identified time intervals. Since the amplitude of the RF ablation signal is small at these acquisition times, interference from the RF ablation signal to the ECG signal is reduced.

The methods and systems described herein provide an improved detection method of the ECG signals during RF ablation, which eliminates the need for costly high-attenuation filters.

System Description

Figure 1:
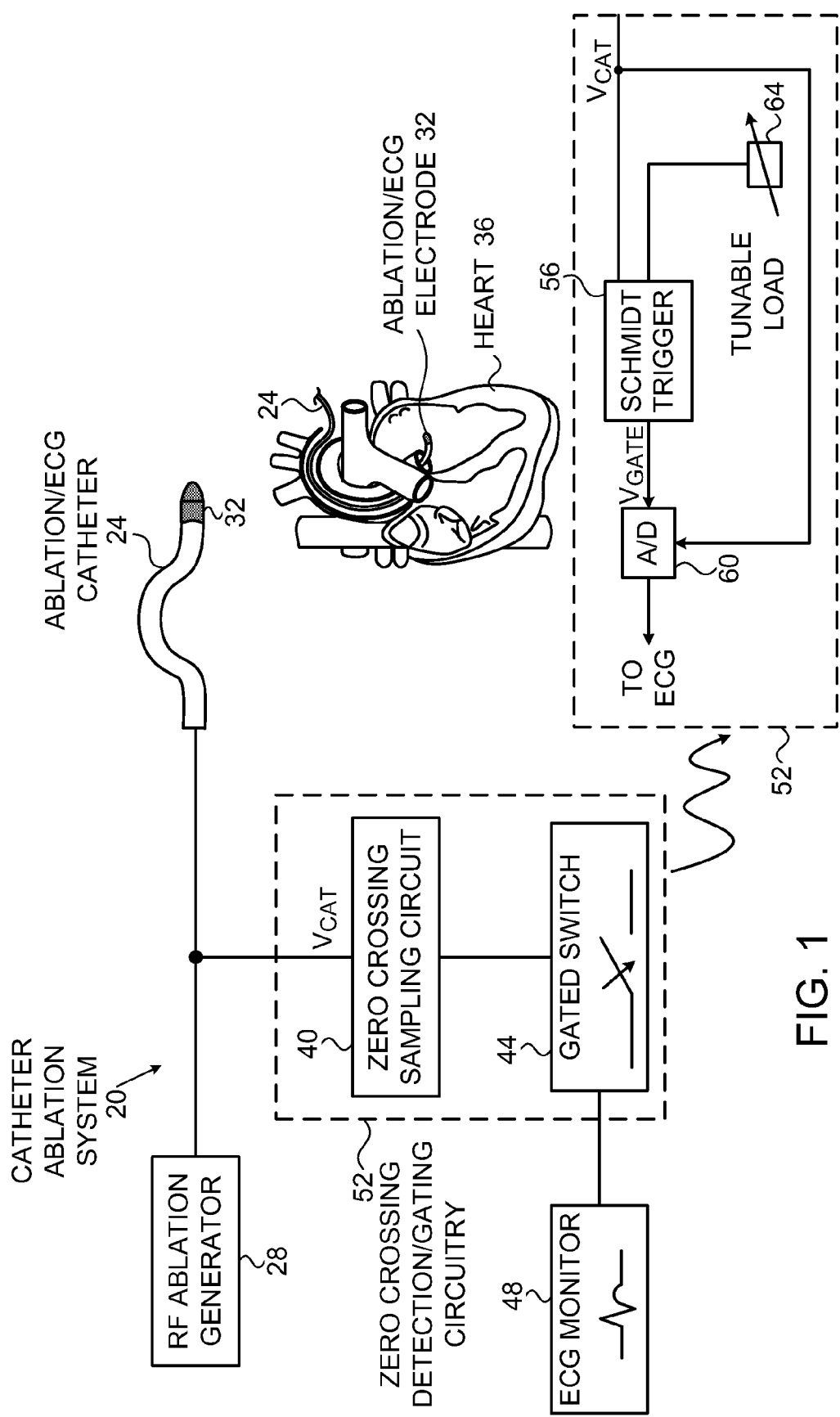
FIG. 1 is a block diagram that schematically illustrates elements of a catheter ablation system, in accordance with an embodiment of the present invention.

FIG. 1 is a block diagram that shows elements of a Catheter Ablation System 20, in accordance with an embodiment of the present invention. An example of Catheter Ablation System 20 is described in "Thermocool Irrigated Tip Catheter and Integrated Ablation System," Biosense Webster Inc. (Diamond Bar, California) product brochure, 2006, which is incorporated herein by reference. Alternatively, system 20 may comprise any other suitable system that conducts RF ablation.

Catheter Ablation System 20 comprises an Ablation/ECG Catheter 24. An RF Ablation Generator 28 applies the RF ablation signal an Ablation/ECG Electrode 32 at the distal tip of Ablation/ECG Catheter 24. Ablation/ECG Catheter 24 is navigated into a Heart 36.

When Ablation/ECG Electrode 32 contacts the tissue of the heart and the RF ablation signal is applied, a lesion is formed in the heart tissue as previously described. During the ablation procedure, Ablation/ECG Electrode 32 also senses electrocardiogram signals. In other embodiments not shown in FIG. 1, the Ablation/ECG catheter may comprise a separate electrode for the ECG signal that is offset from the ablation electrode. Further alternatively, the ablation and ECG electrodes may be fitted in separate catheters in heart 36. Nevertheless, coupling or leakage of the RF ablation signal into the ECG electrode would still corrupt the detected ECG signal.

The catheter signal (denoted Vcat in the figure) thus comprises a superposition of both the RF ablation signal and the sensed ECG signal. However, the RF ablation signal is typically considerably stronger than the sensed ECG signal. In one example scenario, the RF ablation signal is on the order of 170V, while the sensed ECG signal is on the order of 70 μV.

In the embodiments of the present invention shown in FIG. 1, Catheter Ablation System 20 also comprises a Zero Crossing Detection/Gating Circuitry 52 comprising a Zero Crossing Sampling Circuit 40 and a Gated Switch 44. The RF ablation signal is sampled by Circuit 40 for detecting the points of the zero-crossing of the RF ablation signal for identifying the time intervals where the instantaneous RF power is small—Within a predefined window. Circuit 40 produces a gating signal used to open or close switch 44. When gated with the gating signal, switch 44 is closed during the identified time intervals and open otherwise.

Within these time intervals, catheter signal Vcat from Ablation/ECG Catheter 24 is then sampled at the zero crossing of the RF ablation signal precisely where the RF ablation signal power is minimal, effectively separating the component of the ECG signal from the RF ablation signal. A clean ECG signal can be then be displayed on an ECG Monitor 48 with little or no additional filtering, in accordance with the embodiments of this invention.

In some embodiments as shown in FIG. 1, Zero Crossing Detection/Gating Circuitry 52 can be implemented by the use of a Schmidt Trigger 56 and an Analog-to-Digital (A/D) Converter 60. Catheter signal Vcat enters both Schmidt Trigger 56 and A/D 60. Schmidt Trigger 56 comprises a Tunable Load 64, which is used for setting the predefined window around the ablation signal zero crossing.

The system configuration described in FIG. 1 is chosen purely for sake of conceptual clarity. In alternative embodiments, any other suitable system configuration can be used. For example, detection circuitry 52 is not limited to a Schmidt Trigger and an analog-to-digital converter, and can be implemented by other techniques.

Figure 2A:
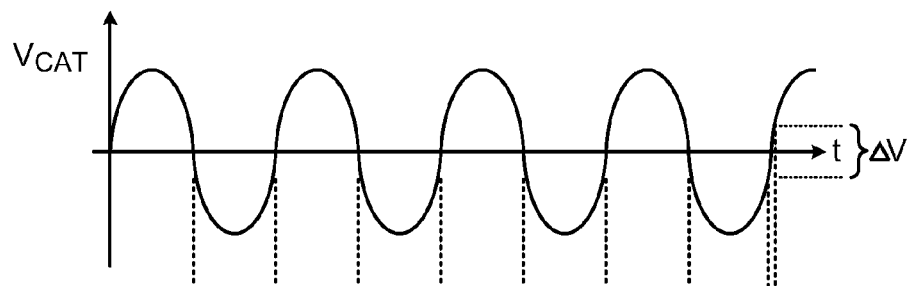
FIGS. 2A and 2B are signal diagrams that schematically illustrate generation of an ECG gating signal based on detection of ablation signal zero crossing, in accordance with an embodiment of the present invention.
Figure 2B:
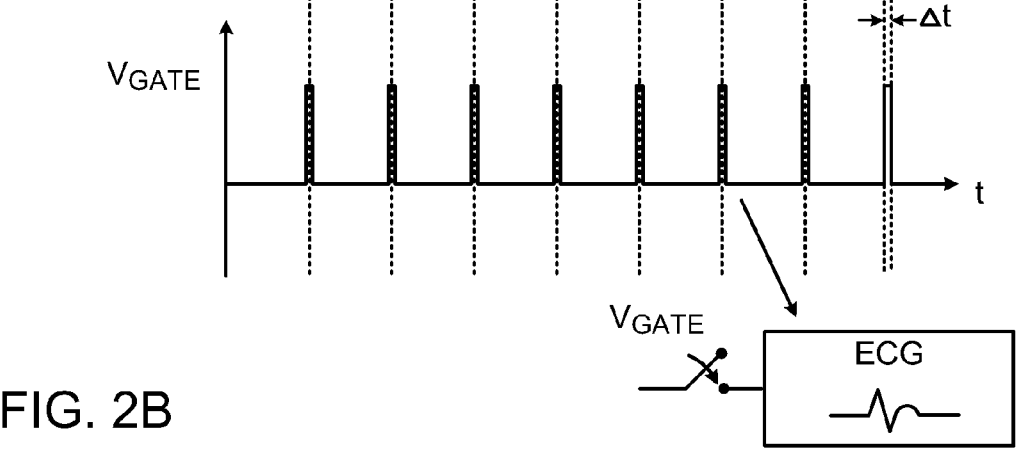

FIGS. 2A and 2B are signal diagrams that schematically illustrate generation of the ECG gating signal based on detection of ablation signal zero crossing, in accordance with an embodiment of the present invention. FIGS. 2A and 2B show the catheter and gating signal waveforms, respectively, on the same time scale. As shown in FIG. 2A, catheter signal Vcat comprising the RF ablation signal and the negligibly small ECG signal as a function of time t has a respective zero-crossing point within each voltage window $\Delta V$.

The magnitude of $\Delta V$ is fixed by the value of Tunable Load 64 of FIG. 1. In this implementation, the Schmidt trigger generates the gating signal based on a comparison between Vcat and the voltage on the tunable load. The output of Schmidt trigger 56 as shown in FIG. 2B is a pulse train waveform Vgate, whose pulse width $\Delta t$ is determined by the magnitude of $\Delta V$ around the zero crossing point mapped onto the time axis as shown in both FIGS. 2A and 2B.

During the pulse width time intervals $\Delta t$, Vgate enables A/D 60 to sample Vcat during the time intervals around the zero crossing of the RF ablation signal component of Vcat allowing a direct sampling of the ECG signal with nearly no corruption by the RF ablation signal. This is shown conceptually in the inset of FIG. 2B. The level of RF leakage is a function of $\Delta V$, which is controlled by Tunable Load 64. The larger $\Delta V$, the larger the time interval $\Delta t$ which enables the A/D to sample the ECG signals at larger departures away from the zero point crossing of the RF ablation signal, where the instantaneous RF power of the RF ablation signal is higher.

Figure 3:
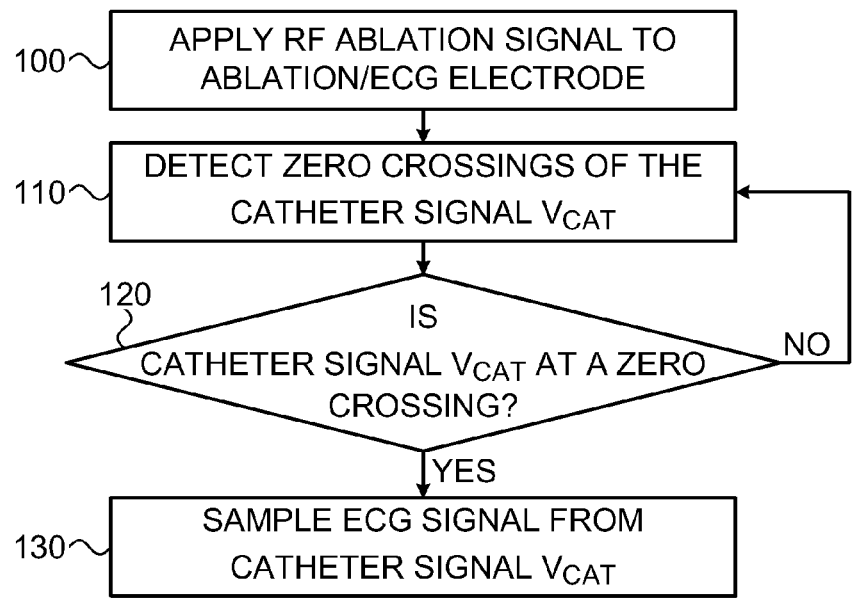
FIG. 3 is a flow chart that schematically illustrates a method for simultaneous RF ablation and ECG sensing, in accordance with an embodiment of the present invention.

FIG. 3 is a flow chart that schematically illustrates a method for simultaneous RF ablation and ECG sensing, in accordance with an embodiment of the present invention. The method begins with RF Ablation Generator 28 applying an RF Ablation signal to Ablation/ECG Electrode 32 at the distal tip of Ablation/ECG Catheter 24, at an RF ablation step 100.

The RF Ablation voltage is the main component of the catheter signal Vcat, which also contains a component of the sensed ECG signal.

At a zero detection step 110, Zero Crossing Sampling Circuit 40 detects the zero crossing of the catheter signal Vcat as shown in FIG. 2A. In other words, circuit identifies the time intervals during which the amplitude of the RF ablation signal is within the predefined window $\Delta V$.

At a decision step 120, circuitry 52 checks if catheter signal Vcat passes through a zero crossing, which is the instantaneous level of zero RF Ablation Power. If so, circuit 40 generates a gating signal pulse as shown in FIG. 2B. Gating signal Vgate closes Gated Switch 44, and catheter signal Vcat is displayed on ECG Monitor 48 through Gated Switch 44 within the time intervals that Gated Switch 44 is closed, at a sampling step 130.

Although the embodiments described herein mainly address the detection of low level ECG signals at the zero crossings of the large signal RF waveforms used during RF ablation therapy, the methods and systems described herein can also be used in other applications, whereby a small biological signal is detected during the zero crossings of RF energy applied to the body during different medical therapies.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   detection circuitry, which is configured to sense a radio frequency (RF) ablation signal that is applied to a heart by an intra-body probe, and to identify time intervals during which an amplitude of an ablation signal is within a predefined window; and
   gating circuitry, which is configured to gate an electrocardiogram (ECG) signal acquired in the heart, such that the ECG signal is sampled only within the identified time intervals.

2. The apparatus according to claim 1, wherein the detection circuitry comprises a Schmidt Trigger configured to generate a gating signal when the amplitude of the RF ablation signal is within the predefined window.

3. The apparatus according to claim 2, and comprising a tunable load for setting the predefined window, wherein the Schmidt Trigger is configured to generate the gating signal based on a comparison between the amplitude of the RF ablation signal and a voltage on the tunable load.

4. The apparatus according to claim 1, wherein the gating circuitry comprises an analog-to-digital converter that is gated to sample the electrocardiogram (ECG) signal only during the identified time intervals.

5. A method, comprising:
   sensing a radio frequency (RF) ablation signal that is applied to a heart by an intra-body probe;
   identifying time intervals during which an amplitude of an ablation signal is within a predefined window; and
   gating an electrocardiogram (ECG) signal acquired in the heart, such that the ECG signal is sampled only within the identified time intervals.

6. The method according to claim 5, wherein gating the ECG signal comprises generating a gating signal using a Schmidt Trigger when the amplitude of the RF ablation signal is within the predefined window.

7. The method according to claim 6, and comprising setting the predefined window using a tunable load, wherein generating the gating signal comprises producing the gating signal by the Schmidt Trigger based on a comparison between the amplitude of the RF ablation signal and a voltage on the tunable load.

8. The method according to claim 5, wherein gating the ECG signal comprises gating an analog-to-digital converter to sample the ECG signal only during the identified time intervals.

9. A cardiac ablation apparatus, comprising:
   a radio frequency (RF) ablation generator, which is configured to generate an RF ablation signal;
   at least one intra-body probe for applying the RF ablation signal in a heart and for acquiring an electrocardiogram (ECG) signal in the heart; and
   a detection and gating unit, comprising:
      detection circuitry, which is configured to sense the RF ablation signal that is applied by the intra-body probe, and to identify time intervals during which an amplitude of the RF ablation signal is within a predefined window; and
      gating circuitry, which is configured to gate the ECG signal acquired in the heart, such that the ECG signal is sampled only within the identified time intervals.

* * * * *